United States Patent [19]

Bertocchio et al.

[11] Patent Number: 5,268,516

[45] Date of Patent: Dec. 7, 1993

[54] SYNTHESIS OF PERFLUOROALKYL IODIDES

[75] Inventors: René Bertocchio, Vourles par Vernaison; Georges Lacote, Chauffailles; Christophe Verge, Bernay, all of France

[73] Assignee: Elf Atochem S.A., France

[21] Appl. No.: 3,767

[22] Filed: Jan. 13, 1993

[30] Foreign Application Priority Data

Jan. 13, 1992 [FR] France .................. 92 00261

[51] Int. Cl.$^5$ ............... C07C 17/04; C07C 21/185
[52] U.S. Cl. ........................ 570/139; 570/123; 570/124; 570/134; 570/138
[58] Field of Search ............ 570/123, 124, 134, 139, 570/138, 126

[56] References Cited

U.S. PATENT DOCUMENTS

| | | | |
|---|---|---|---|
| 3,219,712 | 11/1965 | Hamptschein et al. | 570/139 |
| 3,226,449 | 12/1965 | Blanchard et al. | 570/139 |
| 3,404,189 | 11/1968 | Blochl | 570/139 |
| 3,557,224 | 1/1971 | Jaeger | 570/139 |
| 3,883,604 | 5/1975 | Rudolph et al. | 570/139 |
| 3,956,412 | 5/1976 | Knell | 570/139 |
| 4,067,916 | 1/1978 | Jaeger | 570/139 |
| 5,015,790 | 5/1991 | Hung | 570/126 |

FOREIGN PATENT DOCUMENTS

1096687  7/1967  United Kingdom ......... 570/139

OTHER PUBLICATIONS

European Search Report (Rapport de Recherche) dated Oct. 7, 1992.

*Primary Examiner*—Werren B. Lone
*Attorney, Agent, or Firm*—Morgan & Finnegan

[57] ABSTRACT

The invention relates to a continuous process for the preparation of perfluoroalkyl iodides containing from 4 to 12 carbon atoms by thermal telomerization of tetrafluoroethylene by pentafluoroethyl iodide or heptafluoroisopropyl iodide in a tubular reactor.

According to the invention, 30 to 75% of the tetrafluoroethylene is supplied at the head of the reactor; the remainder is introduced at a point in the reactor located between the 2/5 and ¾ of the length of the tube.

The proportion of undesirable heavy telomers is reduced in this way.

11 Claims, No Drawings

SYNTHESIS OF PERFLUOROALKYL IODIDES

FIELD OF THE INVENTION

The present invention relates to the field of perhalogenated aliphatic hydrocarbons and more particularly relates to the preparation of perfluoroalkyl iodides RfI in which the perfluoroalkyl radical Rf, which may be straight-chain or branched, contains from 4 to 12 carbon atoms

BACKGROUND OF THE INVENTION

Perfluoroalkyl iodides corresponding to the empirical formula $C_nF_{2n+1}I$ where n denotes the number of carbon atoms (or degree of carbon condensation) are used as synthesis intermediates for numerous applications relating in general to the field of fluorinated surface-active substances and more particularly the bases for extinguisher formulations, hydrophobic and oleophobic finishes for the treatment of textiles or of paper, and more recently for applications of a medical nature (contrast agents or oxygen carriers).

Perfluoroalkyl iodides are obtained by telomerization of tetrafluoroethylene (taxogen) by pentafluoroethyl iodide $C_2F_5I$ (telogen), which itself is prepared by the action of iodine and iodine pentafluoride on tetrafluoroethylene in the presence of a catalyst. These two reactions may be coupled as described in French Patent FR 1 385 682, but in the majority of cases $C_2F_5I$ is first prepared and is then used in the telomerization which leads to straight-chain perfluoroalkyl iodides. In order to gain access to branched perfluoroalkyl iodides, a secondary perfluoroalkyl iodide, such as heptafluoroisopropyl iodide $CF_3CFICF_3$, is used as telogen.

The telomerization reaction may be carried out in accordance with at least three methods, the essential difference between which lies in the mode of activation, which may be:

either free radical, with the aid of diverse peroxide initiators, such as in the processes which are the subject of French Patents FR 2 035 913, FR 2 325 665 and U.S. Pat. No. 3,226,449, or catalytic, by the involvement of a redox system as in the processes according to French Patents FR 2 028 781 and FR 2 098 335, or, finally, thermal, as in the processes which are the subject of French Patent FR 1 415 498 and U.S. Pat. No. 3,404,189.

In all of these processes a more or less wide distribution of different chain lengths is obtained and, even in the processes using catalytic initiation which are said to be more selective, it is difficult to attain relatively narrow distributions for telomers of class i ranging from 2 to 5, i denoting the number of molecules of tetrafluoroethylene telomerized by the telogen.

When these perfluoroalkyl iodides are used as synthesis intermediates, the heavier telomers (those of class i>5) are less soluble in the conventional reaction mixtures and have reaction kinetics distinctly slower than those of the more lightweight telomers ($1 \leq i \leq 5$). This results in an adverse accumulation of unconverted intermediates throughout the chain of reactions leading to the final product, with a direct influence on the quality of the latter, in particular in the applications making use of its physicochemical properties, such as, for example, the surfactant activity.

British Patent 1 314 668 describes a process for separating off telomers having a degree of carbon condensation of less than 14 by extraction with the aid of a solvent. This method gives rise to a loss of products and is therefore not satisfactory from the economic standpoint.

One process for reducing the proportion of heavy telomers (>C12) consists in increasing the telogen/taxogen ratio (see French Patents FR 2 028 781 and FR 2 035 913), but this implies a low degree of conversion of the telogen with high recycle ratios and leads to a distribution selectively oriented towards the telomer of class 1. Thus, according to French Patent FR 2 035 913, the telomerisation of $C_2F_4$ by $C_2F_5I$ in a $C_2F_5I/C_2F_4$ ratio of 2.9 leads to the following distribution:

| CLASS | TELOMER | % |
|---|---|---|
| 1 | $C_4F_9I$ | 42.2 |
| 2 | $C_6F_{13}I$ | 23.8 |
| 3 | $C_8F_{17}I$ | 14.6 |
| 4 | $C_{10}F_{21}I$ | 8.64 |
| 5 | $C_{12}F_{25}I$ | 6.25 |
| $\geq 6$ | $\geq C_{14}$ | 4.52 |

It is also possible to modify the reaction time and the degree of conversion of the taxogen. In general, low degrees of conversion improve the selectivity for the class 1 telomer. In practice, the multiplicity of steps which would be necessary to obtain a class i telomer in a selective manner leads to a complex technology and to a result which is equivalent in respect of the proportion of heavy products. In the processes which operate continuously, the optimization for a class i telomer is achieved by complete or partial recycling of the telomers of class i-k where $1 \leq k \leq i-1$.

Now, numerous applications make use of telomers belonging to the $C_6$–$C_{12}$, and more particularly $C_8$–$C_{10}$, cut. The above processes do not permit optimization of the production of RfI telomers for this cut without inevitably increasing the concentration of heavy products.

DESCRIPTION OF THE INVENTION

The aim of the present invention is, therefore, to reduce the proportion of non-valorizable telomers ($C_{14}$ and higher telomers).

It is, moreover, well known that the telomerization of perfluoroalkyl iodides is a very particular telomerization in the sense that each of the telomers formed may in turn act as telogen and thus contribute to the lengthening of the chains, which function in conventional telomerization is virtually exclusively ensured by propagation reactions.

On carrying out telomerizations of tetrafluoroethylene from perfluoroalkyl iodides having various degrees of carbon condensation it was found, surprisingly, that the iodide $C_2F_5I$ leads to very much wider distributions than those obtained with its higher homologues such as $C_4F_9I$, $C_6F_{13}I$, and the like. Thus, the telomerization of tetrafluoroethylene carried out using, successively, $C_2F_5I$, $C_4F_9I$ and $C_6F_{13}I$ as telogen leads, for a telogen/$C_2F_4$ molar ratio of 2.5 and all other things being equal, to the following distributions:

| Starting telogen | Telomers formed (molar %) of class: | | | | |
|---|---|---|---|---|---|
| | 1 | 2 | 3 | 4 | 5 |
| $C_2F_5I$ | 67.5 | 21.9 | 7.1 | 2.3 | 0.8 |
| $C_4F_9I$ | 75.3 | 18.8 | 4.5 | 1.1 | 0.3 |

| Starting | Telomers formed (molar %) of class: | | | | |
|---|---|---|---|---|---|
| telogen | 1 | 2 | 3 | 4 | 5 |
| $C_6F_{13}I$ | 77.4 | 17.8 | 3.8 | 1.0 | <0.1 |

Starting from this observation, it has now been found that, in the continuous of perfluoroalkyl iodides by thermal telomerization of tetrafluoroethylene by pentafluoroethyl iodide or heptafluoroisopropyl iodide, it is possible to reduce the proportion of undesirable heavy telomers by means of a stepped feed of tetrafluoroethylene, that is to say by introducing only a fraction of the tetrafluoroethylene at the head of the reaction, the remainder being introduced at a point in the reactor where the concentration of higher homologues in the reaction mixture has become sufficient to accelerate the transfer reactions.

The process according to the invention, which is carried out in a tubular reactor, is therefore characterized in that it comprises a twin feed of tetrafludroethylene, the first feed at the head of the reactor and the second at at least one point in the reactor located between 2/5 and ¾ of the length of the tube, preferably located at about ⅔ the length of the tube.

Although it is preferred to effect the second $C_2F_4$ feed at a single point located between the 2/5 and ¾ of the length of the tube, it would not go beyond the scope of the present invention to effect this second $C_2F_4$ feed at several points located within the said zone of the tube.

The proportion of tetrafluoroethylene fed in at the head of the reactor may range from 30 to 75% (preferably 40 to 60%) with respect to the total amount of tetrafluoroethylene used.

The overall molar ratio:

$$\frac{telogen}{total\ C_2F_4}$$

may range from 1 to 3 and is preferably between 1.1 and 2.

The telomerization reaction may be carried out in a temperature range ranging from 300° to 360° C., but it is advantageously carried out at a temperature of between about 325° and 355° C.

Industrially, it is preferred to operate under atmospheric pressure, but it would not go beyond the scope of the present invention to operate at a pressure higher than atmospheric pressure, provided that the reaction system remains in the gaseous state.

A contact time of between 10 and 70 seconds is generally suitable, but industrially contact times ranging from 30 to 60 seconds are preferred.

In a continuous process, the degrees of conversion of the telogen are rarely quantitative and this implies the recycling of a more or less large amount of unconverted telogen or of a mixture of the latter with telomers having an average class lower than that of the desired telomers. The process according to the invention also applies to this case.

EXAMPLES

The following examples illustrate the invention without restricting it.

EXAMPLE 1

An empty stainless-steel tubular reactor which is 20 m long and has an internal diameter of 4 mm is used. It is kept at a temperature of 344±5° C. by means of a suitable device and at its mid-length it has a tap which can be isolated by means of a valve.

1a: A gas stream of $C_2F_5I$ (0.349 mol/h) and $C_2F_4$ (0.277 mol/h) is fed in at the head of this reactor. The reaction products are collected at the reactor outlet in liquid or gaseous form by trapping. Analysis of these products shows that 2.3% of the telomers formed (mol%) have a carbon condensation higher than 12.

1b: The same reactor is used, but all of the $C_2F_5I$ and only 75% (0.208 mol/h) of the $C_2F_4$ are introduced at the head. The remainder of the $C_2F_4$ (0.069 mol/h) is introduced by the side tap midway along the length of the tube. Under these conditions, the proportion of telomers having a carbon condensation higher than 12 falls to 1.7%.

1c: Experiment 1b is repeated introducing only 50% of the $C_2F_4$ at the head of the reactor with all of the $C_2F_5I$, the remainder of the $C_2F_4$ entering by the side tap. The product collected at the reactor outlet contains no more than 0.9% of telomers higher than $C_{12}F_{25}I$.

The following table specifies the operating conditions and the results of these three experiments.

| EXPERIMENT | 1a comparative | 1b | 1c |
|---|---|---|---|
| % of $C_2F_4$ introduced at the head of the reactor | 100 | 75 | 50 |
| Total molar ratio | | | |
| $C_2F_5I/C_2F_4$ | 1.26 | 1.22 | 1.26 |
| Contact time (seconds) | 59 | 60.5 | 60.9 |
| Temperature (°C.) | 344 | 344 | 344 |
| Degree of conversion of $C_2F_4$ (%) | 73.3 | 69.7 | 62.8 |
| Telomer distribution (mol %) | | | |
| $C_4$ | 53.2 | 54.4 | 56.8 |
| $C_6$ | 24.7 | 24.6 | 24.8 |
| $C_8$ | 11.6 | 11.1 | 10.5 |
| $C_{10}$ | 5.3 | 6.0 | 5.2 |
| $C_{12}$ | 2.7 | 2.1 | 1.6 |
| $>C_{12}$ | 2.3 | 1.7 | 0.9 |

EXAMPLE 2

The three experiments of Example 1 are repeated, but positioning the side tap at 2/3 the length of the tube (or 13.33 m from the inlet).

On introducing half of the $C_2F_4$ through this tap (experiment 2c), the content of heavy telomers is reduced to 0.7%.

The following table specifies the operating conditions and the results of these three experiments.

| EXPERIMENT | 2a comparative | 2b | 2c |
|---|---|---|---|
| % of $C_2F_4$ introduced at the head of the reactor | 100 | 75 | 50 |
| Total molar ratio | | | |
| $C_2F_5I/C_2F_4$ | 1.22 | 1.21 | 1.25 |
| Contact time (seconds) | 60.6 | 60.3 | 59.5 |
| Temperature (°C.) | 344 | 344 | 344 |
| Degree of conversion of $C_2F_4$ (%) | 74.25 | 66.3 | 54.2 |
| Telomer distribution (mol %) | | | |

-continued

| EXPERIMENT | 2a comparative | 2b | 2c |
|---|---|---|---|
| $C_4$ | 52.9 | 56.0 | 60.6 |
| $C_6$ | 24.0 | 24.5 | 23.9 |
| $C_8$ | 11.2 | 10.6 | 9.2 |
| $C_{10}$ | 7.6 | 5.5 | 4.4 |
| $C_{12}$ | 2.4 | 1.9 | 1.2 |
| $>C_{12}$ | 1.9 | 1.6 | 0.7 |

EXAMPLE 3

The reactor used in Example 2 (side tap at the ⅔ length) is fed with a mixture containing 75.8% of $C_2F_5I$ and 24.2% of $C_4F_9I$ (mol%)

3a: The reaction is carried out at 344° C. and all of the tetrafluoroethylene is introduced at the head of the reactor, the total molar ratio of telogens/$C_2F_4$ being substantially the same as in the preceding examples.

Under these conditions, the proportion of heavy telomers reaches 1.82% for a degree of conversion of $C_2F_4$ of 76.6%.

3b: The reaction is likewise carried out at 344° C., but 50% of the $C_2F_4$ is introduced at the head of the tube and the remainder at the 2/3 length of the tube.

The proportion of heavy telomers does not exceed 0.53% with a degree of conversion of $C_2F_4$ of 58.5%.

3c: Experiment 3b is repeated, but carrying out the reaction at 355° C. The degree of conversion of the $C_2F_4$ rises again to 73.9% for a heavy telomer content of 0.76%.

The following table specifies the operating conditions and the results of these three experiments.

| EXPERIMENT | 3a comparative | 3b | 3c |
|---|---|---|---|
| % of $C_2F_4$ introduced at the head of the reactor | 100 | 50 | 50 |
| Total molar ratio | | | |
| $(C_2F_5I + C_4F_9I)/C_2F_4$ | 1.27 | 1.31 | 1.22 |
| Contact time (seconds) | 59.5 | 59.9 | 60.2 |
| Temperature (°C.) | 344 | 344 | 355 |
| Degree of conversion of $C_2F_4$ (%) | 76.6 | 58.5 | 73.9 |
| Telomer distribution (mol %) | | | |
| $C_4$ | 53.4 | 58.3 | 54.4 |
| $C_6$ | 25.0 | 25.9 | 27.2 |
| $C_8$ | 11.5 | 10.1 | 11.7 |
| $C_{10}$ | 6.0 | 4.05 | 4.46 |
| $C_{12}$ | 2.25 | 1.14 | 1.46 |
| $>C_{12}$ | 1.82 | 0.53 | 0.76 |

Comparison of experiments 3a and 3c shows that, for a substantially equal degree of conversion, the stepped introduction of the $C_2F_4$ makes it possible advantageously to reduce the proportion of heavy telomers which are difficult to valorize.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim

1. Continuous process for the preparation of perfluoroalkyl iodides containing from 4 to 12 carbon atoms comprising thermal telomerization of tetrafluoroethylene by pentafluoroethyl iodide or heptafluoroisopropyl iodide in a tubular reactor, a twin feed of tetrafluoroethylene, the first feed at the head of the reactor and the second at least one point in the reactor located between 2/5 and ⅔ of the length of the tube, the proportion of tetrafluoroethylene fed in at the head representing 30 to 75% of the total amount of tetrafluoroethylene used.

2. Process according to claim 1, wherein the second feed of tetrafluoroethylene is effected at a point in the reactor located at approximately ⅔ of the length of the tube.

3. Process according to claim 1, wherein the proportion of tetrafluoroethylene fed in at the head represents 40 to 60% of the total amount of tetrafluoroethylene used.

4. Process according to claim 1, wherein the total molar ratio: telogen/total $C_2F_4$ is between 1 and 3.

5. Process according to claim 1, wherein the telomerization is carried out at a temperature ranging from 300 to 360° C.

6. Process according to claim 1, wherein the reaction is carried out under atmospheric pressure.

7. Process according to claim 1, wherein the contact time is between 10 and 70 seconds.

8. Process according to claim 1, wherein the unconverted pentafluoroethyl iodide or heptafluoroisopropyl iodide or a mixture of the latter with telomers having an average class lower than that of the desired telomers is recycled to the reactor head.

9. Process according to claim 4, wherein the molar ratio is between 1.1 and 2.

10. Process according to claim 5, wherein the temperature is between about 325° and 355° C.

11. Process according to claim 7, wherein the contact time is between 30 and 60 seconds.

* * * * *